(12) United States Patent
Esquivel de la Garza

(10) Patent No.: US 10,466,162 B2
(45) Date of Patent: Nov. 5, 2019

(54) MANUALLY OR REMOTELY-CONTROLLED ROLLING-BALL APPARATUS FOR MEASURING INSTANTANEOUS ADHESION

(71) Applicant: DYNASOL ELASTÓMEROS, S.A. DE C.V., Altamira, Tamaulipas (MX)

(72) Inventor: Alejandro Claudio Esquivel de la Garza, Tamaulipas (MX)

(73) Assignee: DYNASOL ELASTÓMEROS, S.A. DE C.V., Altamira, Tamaulipas (MX)

( * ) Notice: Subject to any disclaimer, the term of this patent is extended or adjusted under 35 U.S.C. 154(b) by 216 days.

(21) Appl. No.: 15/532,831

(22) PCT Filed: Dec. 2, 2014

(86) PCT No.: PCT/MX2014/000190
§ 371 (c)(1),
(2) Date: Jun. 2, 2017

(87) PCT Pub. No.: WO2016/089189
PCT Pub. Date: Jun. 9, 2016

(65) Prior Publication Data
US 2017/0370824 A1 Dec. 28, 2017

(51) Int. Cl.
*G01N 19/04* (2006.01)
*G01N 19/00* (2006.01)
(Continued)

(52) U.S. Cl.
CPC ............ *G01N 19/04* (2013.01); *B60G 15/02* (2013.01); *B65G 53/50* (2013.01); *G01N 3/56* (2013.01);
(Continued)

(58) Field of Classification Search
None
See application file for complete search history.

(56) References Cited

U.S. PATENT DOCUMENTS

| 5,635,623 A * | 6/1997 | Simon ................ G01M 17/02 73/146 |
| 7,306,524 B1 | 12/2007 | Rogers |

(Continued)

FOREIGN PATENT DOCUMENTS

WO 95/32033 A1 5/1995

OTHER PUBLICATIONS

International Search Report and Written Opinion of the International Searching Authority for corresponding International Patent Application No. PCT/MX2014/000190 dated Jul. 6, 2015, 7 pgs.

*Primary Examiner* — Clayton E. LaBalle
*Assistant Examiner* — Dennis Hancock
(74) *Attorney, Agent, or Firm* — Merchant & Gould P.C.

(57) ABSTRACT

A measuring apparatus to measure adhesive performance of a Pressure Sensitive tape or label, which includes an electric or pneumatic actuator that can be triggered manually or remotely to perform a rolling ball tack evaluation at different or extreme conditions to those standardized in an adhesives laboratory, by using a small laboratory oven or small weathering chamber to simulate those extreme conditions. Also, installing this apparatus inside of those chambers and triggering it remotely through the mentioned actuator installed in the apparatus. The triggering systems includes; a power source to convert the standard laboratory high voltage source to low DC voltage to avoid the risk of an electric shock during the apparatus operation, a couple of metallic isolated cables for electric conduction of voltage to the actuator electric coil, an electric control box containing a momentary push button switch, the actuator containing an electric coil, a spring and a metallic mobile piston, and a mechanical fastening system to attach the actuator to the apparatus and the piston to the mechanical ball release system.

15 Claims, 3 Drawing Sheets

(51) Int. Cl.
*B60G 15/02* (2006.01)
*B65G 53/50* (2006.01)
*G01N 3/56* (2006.01)
*G01N 19/02* (2006.01)

(52) U.S. Cl.
CPC ............ *G01N 19/00* (2013.01); *G01N 19/02* (2013.01); *G01N 2203/0091* (2013.01); *G01N 2203/0282* (2013.01)

(56) References Cited

U.S. PATENT DOCUMENTS 8,069,702 B2 * 12/2011 Zhang .................... G01N 19/04
73/150 A
2009/0100928 A1  4/2009 Fry et al.

* cited by examiner

MANUALLY OR REMOTELY-CONTROLLED ROLLING-BALL APPARATUS FOR MEASURING INSTANTANEOUS ADHESION

This application is a National Stage Application of PCT/MX2014/000190, filed 2 Dec. 2014, and which application is incorporated herein by reference. To the extent appropriate, a claim of priority is made to the above disclosed application.

TECHNICAL FIELD

The present disclosure relates to a measuring apparatus to measure adhesion performance of adhesives when they are impregnated as a layer on the surface of a film to be used as tape, label or other bonding system.

BACKGROUND OF THE INVENTION

In Pressure Sensitive Tapes and labels manufacture, it is very important to use an adhesive according to the final application to obtain the desired performance. The adhesives formulator has several ways to adjust the final adhesive properties to fulfill those requirements, starting from balancing the composition's formula up to changing some ingredients like Polymers, Tackifiers etc.

Some applications, like packaging, require high shear and cohesive strength to maintain the integrity of the content, but when an automated application system is used, a fast adhesion is very important for productivity.

When tapes and labels are required to perform at different conditions than the room or standardized laboratory conditions, according to specifications for standardized test methods, it is necessary to develop specific evaluations at those mentioned different conditions.

Standardized systems like ASTM, PSTC, among others, describe several standardized analytical techniques to characterize all the adhesive properties, most of them are performed at standardized room conditions of 23° C. and 50% of relative humidity, and others are performed at higher temperatures or higher humidity contents for applications, wherein the adhesive is exposed at such conditions.

Rolling ball tack is a preferred test for adhesion performance of adhesive used in applications like tapes and labels when a fast bonding procedure is going to be used. This evaluation is performed using a metallic ball which rolls at constant speed over the adhesive surface of the tape or label to be evaluated. The impulse of the metallic ball, to reach constant speed, is obtained using a metallic standardized ramp with a constant slope angle, over which the ball rolls to reach the surface of the adhesive in the tape or label. The higher the adhesion performance for the adhesive is, the shorter the metallic ball travel will be, and vice versa. The operation to liberate the ball in the top of the ramp, is made manually by an operator who pushes the trigger of the mechanism which retains the ball.

However, test methods and equipments for this evaluation are just referred to be performed at standardized conditions according to PSTC, ASTM and other standardized evaluation methods.

In other words, it is known that the Pressure Sensitive Adhesives, reduce their tack performance when the room temperature is reduced. Thus, when tapes or labels are going to be applied at temperatures below room temperature, it is very important to know if the adhesive maintains enough adhesion at those temperature conditions, to reach an adequate speed of bonding process.

When Rolling ball tack evaluations need to be performed at reduced temperatures, some adhesive producers develop this evaluation in a specific conditioned room, which is equipped with an adequate cooling system to reach the required reduced temperature, and with dimensions that allow an operator to go inside. The operator must be equipped with special clothes to support frozen temperatures in order to operate the ramp and carry out the evaluation. This is an expensive installation to build and uses a considerable amount of energy to operate at the mentioned low temperatures, which increases the cost of the evaluation. Additionally, cooling the room to the evaluation temperature takes several hours, and thus sometimes just one evaluation can be performed every day.

Adhesive formulators are looking for an evaluation system that allows them to develop the rolling ball tack evaluations at under zero temperatures, in a faster way, with reduced installation investment, lower operation costs and operator risks, maintaining evaluation accuracy and repeatability.

U.S. Pat. No. 8,069,702 describes a measuring apparatus to measure adhesion of a tape. The measuring apparatus includes a base, a supporting plate, a positioning mechanism, and an angle-adjusting mechanism. However, the apparatus described in U.S. Pat. No. 8,069,702 does not disclose a remote trigger as the one described in the present invention.

Proposed herein is a new ramp design that can be triggered remotely, generating the possibility of its use inside a small laboratory chamber that can control room conditions of lower temperature and humidity that are required for the aforementioned evaluations. Said new ramp design eliminates the requirement of an expensive cooling room, with all the peripheral equipment and the requirement that the operator must go inside it to operate the system.

SUMMARY OF THE INVENTION

The present invention relates to a measuring apparatus to measure adhesion performance of an adhesive comprising a rolling ball tack equipment, and a triggering system. Said system can be operated remotely to trigger the system that liberates the metallic ball in the superior part of the ramp.

In one embodiment of the invention, the triggering system is an electromagnetic actuator and in another embodiment, the triggering system is a pneumatic actuator. The electromagnetic actuator can be operated remotely by the use of a battery or an equivalent electrical power source In another embodiment, the triggering system of the ramp is a pneumatic actuator fed from the standard laboratory air supply, with a flow and pressure according to the same pneumatic actuator requirements.

The above described embodiments represent an advantage to the adhesives formulators, pressure sensitive tapes and label producers or final users, who have the need of measuring adhesive performance in different conditions to those of the standardized conditions existing in laboratories. This is because the rolling ball tack evaluation can be reproduced by using small conditioned chambers like laboratory ovens, weathering chambers, and similar equipment, that allows the formulator to simulate the special conditions required for some specific final applications, introducing the ramp into these small chambers and firing the electromechanically remote actuator integrated in it, remotely from the outside of the closed chamber.

DETAILED DESCRIPTION

Described herein is a new ramp design to perform the adhesion measurement known as "rolling ball tack" which includes a system that can be operated remotely to trigger the system that liberates the metallic ball in the superior part of the ramp to reach constant speed, and run over the adhesive surface for a distance in function of the adhesion capacity of the adhesive under evaluation.

In one embodiment of the present invention, a new ramp design including a remote triggering system is used to perform the measurement of adhesion known as "rolling ball tack" for a pressure sensitive adhesive impregnated in a film, using a small weathering chamber for use in laboratory, to generate the room temperature and humidity conditions required for the test. Said ramp avoids the requirement of a room and the peripheral equipment and energy required to generate and control the same room conditions inside such room, and avoiding at the same time the requirement that an operator must enter that room at those extreme conditions to develop the test.

In another embodiment, the triggering system of the ramp is an electromagnetic actuator that can be operated remotely by the use of a battery or an equivalent electrical power source, that can be fed from the standard electrical laboratory web (110 VAC, 220 VAC) and has a low direct current output voltage (12 VDC or what applies according to the coil demand of the electromagnetic actuator) to avoid the risk of an electric shock for the equipment operators.

In another embodiment, the triggering system of the ramp is a pneumatic actuator fed from the standard laboratory air supply, with a flow and pressure according to the same pneumatic actuator requirements.

In another embodiment, the electromagnetic or pneumatic actuators can be triggered without the requirement of cables through a wireless electronic transmission-reception system.

Figure 1:
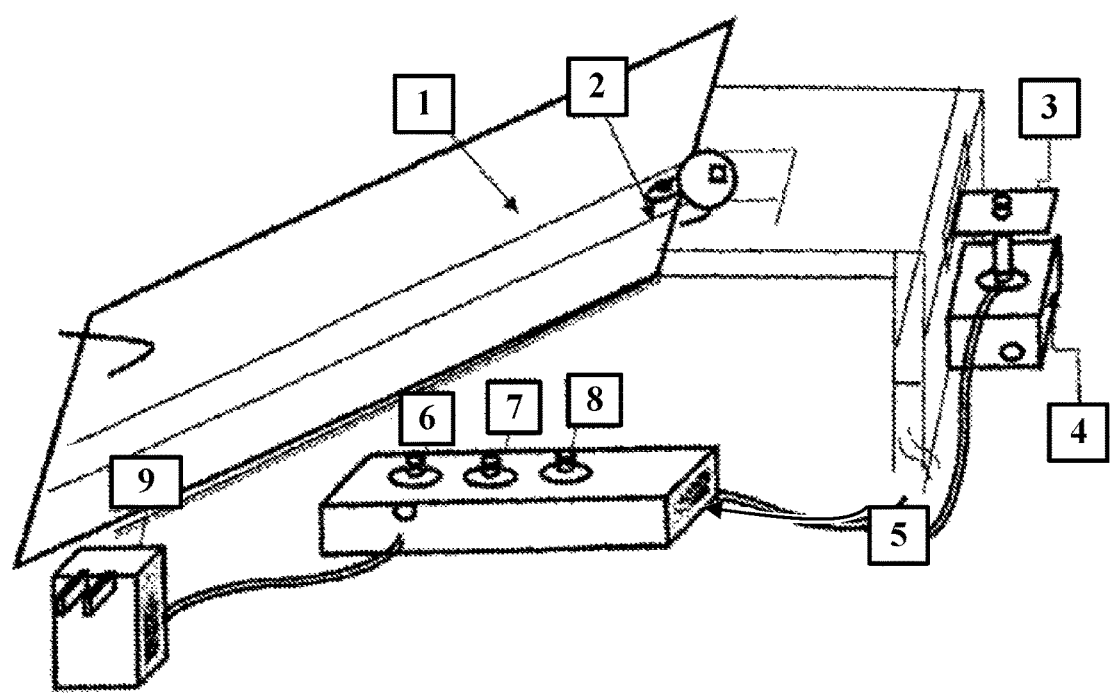
FIG. 1 is a view of the assembled rolling ball tack ramp including a wired electromagnetic actuator, the remote control and the power source.
Figure 2:
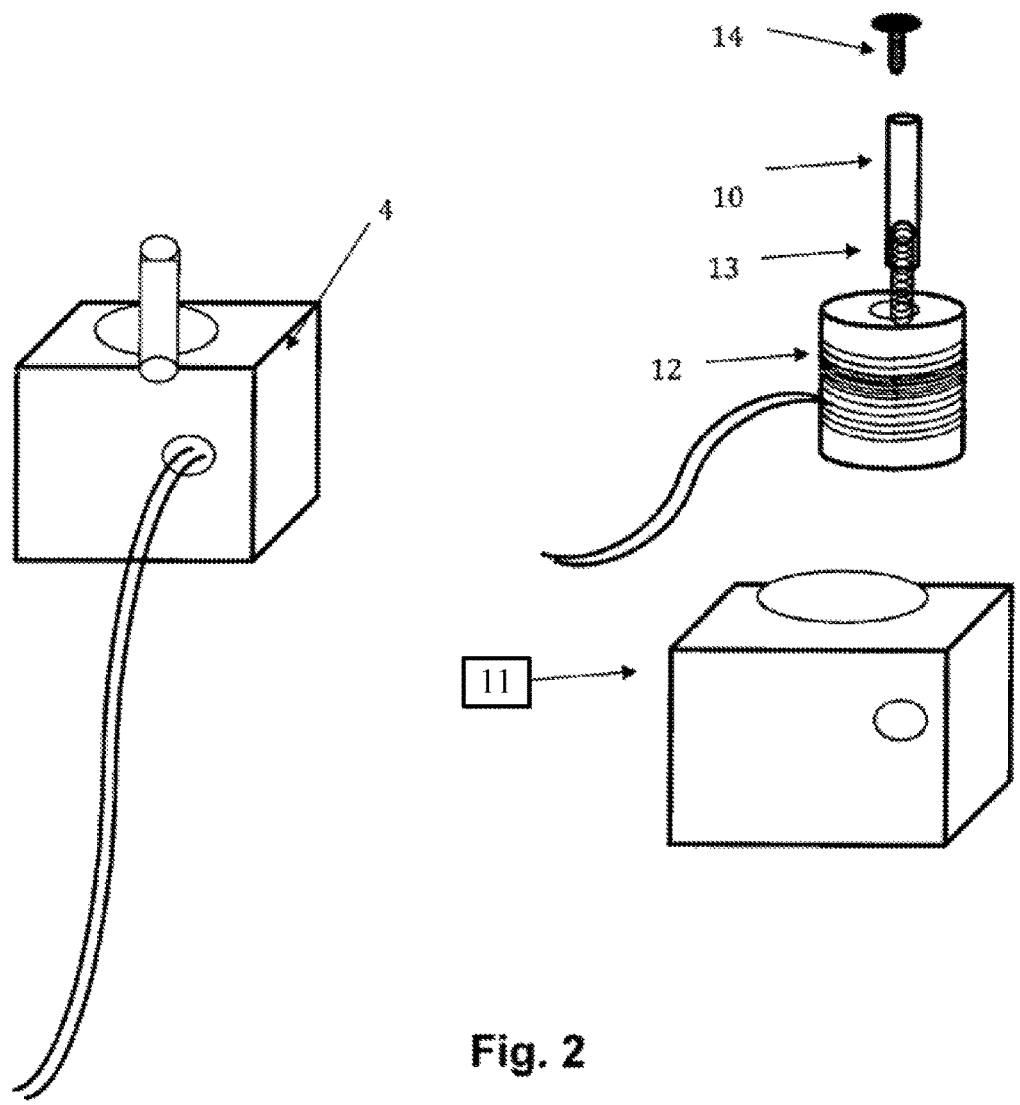
FIG. 2 is an enlarged, exploded view of the electromagnetic actuator mechanism.

FIGS. 1 and 2 show an example of the assembly of an electromagnetic actuator (4) in a standard rolling ball tack equipment (1). The electromagnetic coil is energized by a power supply (9), through a couple of isolated metallic cables for electrical transmission, and controlled by an electronic circuit (5) which contains a momentary push button switch and a couple of light emission diodes (LED), where the first (green) (6) indicates when the system is energized and the second (red) (7) indicates that the actuator is fired.

The electric power supply may be fed from the standard electrical laboratory web (110 VAC, 220 VAC) and has a low DC output voltage (12 VDC or what applies according to the coil demand of the electromagnetic actuator) to avoid the risk of an electric shock for the equipment operators. The green light (6) in the control box (5) will glow when the power supply is energized and ready for operation.

The electromagnetic actuator (4) of this example is basically a solenoid, composed by a 12 VDC electric coil (12), that acts over a metallic piston (10) which is maintained in its upper position by a metallic spring (13), The metallic piston is attached to the metallic ball release system by a screw (14). This assembling is installed in a sealed enclosure (11) to protect it from ambient conditions.

When the electromagnetic actuator's coil (12) is energized through the control system pushing the black switch (8) in the control box (5), with adequate electric power supply (9) (12 VDC for this example), the red light (7) will glow, and the metallic piston (10) is attracted down into the coil cavity compacting the spring (13) into the coil cavity, and firing at the same time the ball release system (3) to start the test.

The above described embodiment, represents an advantage to the adhesives formulators, pressure sensitive tapes an label producers, or final users, who have the need of measuring adhesive performance in different conditions to those of the standardized conditions existing in laboratories. Consequently, it is possible to reproduce the rolling ball tack evaluation by using small conditioned chambers like laboratory ovens, weathering chambers, and similar equipment, that allows the formulator to simulate special conditions that are required for some specific final applications, by introducing the ramp into these small chambers and firing the electromechanically remote actuator integrated in it, remotely from the outside of the closed chamber.

Figure 3:
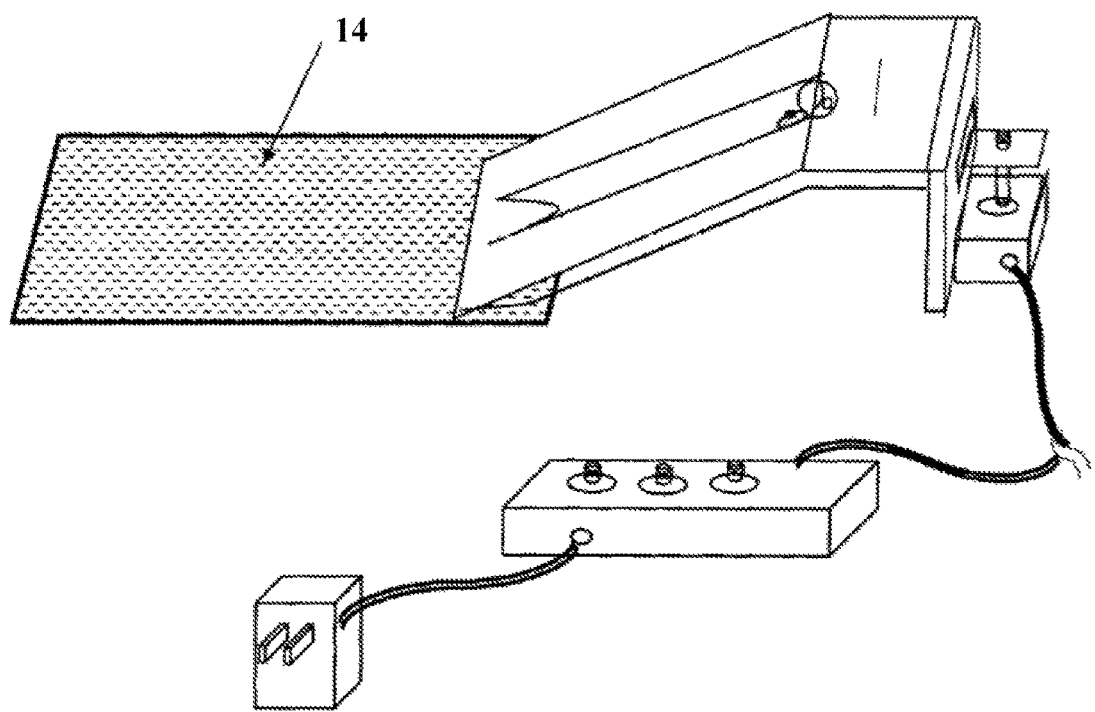
FIG. 3 is a view of the use of the embodiment for measurement of adhesion performance for a pressure sensitive Tape or label.

The embodiment is used as is shown in FIG. 3. That is, the system is mounted over a sample of the pressure sensitive tape or label (14) with the adhesive face upside. The metallic ball is positioned as indicated in FIG. 3, stabilized by the triggering system (2), the power supply is connected to the AC source in the lab, and the test is triggered by pushing the push button momentary switch. The adhesion is inversely proportional to the distance traveled by the metallic ball.

The use of the above described embodiment generates considerable savings by avoiding the requirement of investing in the construction of a specific room with the all the complementary equipment to control extreme temperature and humidity ambient conditions to perform this test. Additional savings are obtained from energy savings from the operation of this big size room.

The invention claimed is:

1. A measuring apparatus for measuring adhesion performance of an adhesive when it is impregnated as a layer on a surface of an article, comprising:
    a rolling ball tack equipment for measuring adhesion performance including a metallic ball and a ramp positioned adjacent the article to be evaluated; and
    a remote triggering system, the remote triggering system including a power source, one or more metallic isolated cables, and an electric control box, wherein said triggering system is installed inside the apparatus and liberates the metallic ball in the superior part of the ramp.

2. The measuring apparatus of claim 1, wherein the remote triggering system is an electromagnetic actuator.

3. The measuring apparatus of claim 2, wherein the electromagnetic actuator is a solenoid, wherein the solenoid includes an electric coil.

4. The measuring apparatus of claim 3, wherein the electric coil is energized by a power supply and is controlled by an electronic circuit.

5. The measuring apparatus of claim 4, wherein the electronic circuit contains a momentary push button switch and one or more light emission diodes (LED), wherein the first light indicates that the system is energized and the second light indicates that the actuator is fired.

6. The measuring apparatus of claim 3, wherein the electric coil acts over a metallic piston that is maintained in an upper position by a metallic spring and wherein said metallic spring is attached to a metallic ball liberation system by a screw.

7. The measuring apparatus of claim 2, wherein the electromagnetic actuator is triggered using a wireless control.

8. The measuring apparatus of claim 1, wherein said apparatus is used in standardized evaluation systems such as PSTC, ASTM, or any other rolling ball test standard.

9. The measuring apparatus of claim 1, wherein said apparatus is used for special evaluations in different conditions than those specified in PSTC, ASTM, or any other rolling ball test standard.

10. The measuring apparatus of claim 1, wherein the article is a pressure sensitive tape or label.

11. A measuring apparatus for measuring adhesion performance of an adhesive when it is impregnated as a layer on a surface of an article, comprising:

a rolling ball tack equipment for measuring adhesion performance including a metallic ball and a ramp positioned adjacent the article to be evaluated; and a remote triggering system, the remote triggering system including a pneumatic actuator, wherein said triggering system is installed inside the apparatus and liberates the metallic ball in the superior part of the ramp.

12. The measuring apparatus of claim 11, wherein the pneumatic actuator is triggered using a wireless control.

13. The measuring apparatus of claim 11, wherein the apparatus is used in standardized evaluation systems such as PSTC, ASTM, or any other rolling ball test standard.

14. The measuring apparatus of claim 11, wherein said apparatus is used for special evaluations in different conditions than those specified in PSTC, ASTM, or any other rolling ball test standard.

15. The measuring apparatus of claim 11, wherein the article is a pressure sensitive tape or label.

* * * * *